United States Patent
Schaefer et al.

(10) Patent No.: US 10,172,986 B2
(45) Date of Patent: Jan. 8, 2019

(54) BLOOD PUMP INTEGRATED IN A HOUSING FRONT

(71) Applicant: B. BRAUN AVITUM AG, Melsungen (DE)

(72) Inventors: Oliver Schaefer, Neuenstein (DE); Kai-Uwe Ritter, Rednitzhembach (DE)

(73) Assignee: B. BRAUN AVITUM AG, Melsungen (DE)

( * ) Notice: Subject to any disclaimer, the term of this patent is extended or adjusted under 35 U.S.C. 154(b) by 441 days.

(21) Appl. No.: 15/046,873

(22) Filed: Feb. 18, 2016

(65) Prior Publication Data

US 2016/0243296 A1 Aug. 25, 2016

(30) Foreign Application Priority Data

Feb. 25, 2015 (DE) .................... 10 2015 102 658

(51) Int. Cl.
| | |
|---|---|
| *A61M 1/10* | (2006.01) |
| *A61M 1/14* | (2006.01) |
| *B01D 61/28* | (2006.01) |

(52) U.S. Cl.
CPC ........ *A61M 1/1043* (2014.02); *A61M 1/1006* (2014.02); *A61M 1/14* (2013.01);
(Continued)

(58) Field of Classification Search
CPC .... B01D 61/243; B01D 61/28; A61M 1/1001; A61M 1/1006; A61M 1/1039;
(Continued)

(56) References Cited

U.S. PATENT DOCUMENTS

| 4,734,184 A | 3/1988 | Burleigh et al. |
| 6,071,095 A | 6/2000 | Verkaart |

(Continued)

FOREIGN PATENT DOCUMENTS

| DE | 697 22 065 | 4/2004 |
| DE | 10 2012 105 913 | 1/2014 |

(Continued)

OTHER PUBLICATIONS

European Search Report for EP 16 155 926.5 dated Jul. 21, 2016, with translation.

(Continued)

*Primary Examiner* — Jason M Greene
(74) *Attorney, Agent, or Firm* — RatnerPrestia

(57) ABSTRACT

A device for extracorporeal blood treatment, in particular a dialysis machine, including a peristaltic pump for conveying fluid from a low-pressure side to a high-pressure side, the peristaltic pump comprising a rotor which is rotatable around a rotor axis and a support area which is formed around the rotor axis in an arcuate manner, with an elastically deformable fluid line being able to be positioned between the rotor and the support area and being deformed between the rotor and the support area with rotation of the rotor while forming a cross-sectional constriction, so that upon rotation of the rotor with respect to the support area a fluid in the fluid line is conveyed from the low-pressure side to the high-pressure side. The device includes a machine housing part realized as a formed sheet metal part, wherein the support area is formed in the machine housing part by plastic deformation.

14 Claims, 3 Drawing Sheets

(52) U.S. Cl.
CPC .......... *B01D 61/28* (2013.01); *A61M 1/1001* (2014.02); *A61M 1/1039* (2014.02); *A61M 2207/00* (2013.01)

(58) Field of Classification Search
CPC .... A61M 1/1041; A61M 1/1043; A61M 1/14; A61M 2207/00; F04B 43/12; F04B 43/123; F04B 43/1261
See application file for complete search history.

(56) References Cited

U.S. PATENT DOCUMENTS

| | | | |
|---|---|---|---|
| 2004/0265154 A1* | 12/2004 | McDowell | F04B 43/009 417/474 |
| 2005/0069437 A1 | 3/2005 | Mittelstein et al. | |
| 2007/0140880 A1* | 6/2007 | Fulmer | F04B 43/1253 417/477.1 |
| 2009/0084717 A1* | 4/2009 | Delmage | A61M 1/34 210/108 |
| 2010/0089806 A1* | 4/2010 | Peters | B01D 61/28 210/90 |
| 2012/0282126 A1* | 11/2012 | Brandt | A61M 1/1037 417/477.9 |
| 2014/0012201 A1 | 1/2014 | Schaefer | |

FOREIGN PATENT DOCUMENTS

| WO | WO 90/06781 | 6/1990 |
|---|---|---|
| WO | WO 97/10436 | 3/1997 |

OTHER PUBLICATIONS

German Search Report for DE 10 2015 102 658.9 dated Aug. 5, 2015, with translation.

* cited by examiner

BLOOD PUMP INTEGRATED IN A HOUSING FRONT

CROSS REFERENCE TO RELATED APPLICATIONS

This application claims priority to German application DE 10 2015 102 658.9 filed Feb. 25, 2015, the contents of such application being incorporated by reference herein.

FIELD OF THE INVENTION

The invention relates to a device for extracorporeal blood treatment, more specifically to a device for extracorporeal blood treatment, in particular dialysis machine, comprising a peristaltic pump for conveying fluid from a low-pressure side to a high-pressure side, said peristaltic pump comprising a rotor which is rotatable around a rotor axis and a support area which is formed around the rotor axis in arcuate manner, with an elastically deformable fluid line being able to be positioned between the rotor and the support area and being deformed between the rotor and the support area with rotation of the rotor while forming a cross-sectional constriction, so that upon rotation of the rotor with respect to the support area a fluid in the fluid line is conveyed from the low-pressure side to the high-pressure side, the device comprising a machine housing realized as a formed sheet metal part.

BACKGROUND OF THE INVENTION

Known peristaltic pumps in medical apparatuses for extracorporeal blood treatment usually consist of a rotor, a pump housing and an elastic hose line as fluid line arranged between the rotor and the pump housing. The pump housing defines a support area for the fluid line. From the prior art, attached blood pump housings are known. By way of example, a pump housing of known peristaltic pumps for such medical apparatuses is made as a separate milled part of aluminum or as an injection-molded plastic part and mounted to a housing front of the apparatus. Implementing the pump housing with a separate component is disadvantageous due to relative high production and storage costs as a result of the additional component. What is more, an assembly process for mounting the pump housing to the machine housing is required, which is time-consuming and expensive. Finally, milled parts with such complex shapes are costly per se. The use of a pump housing made of plastics may indeed produce relief here in part, but at the expense of strength and resistance to wear.

SUMMARY OF THE INVENTION

In the light of the prior art described above, the present invention is based on the object to eliminate the previously mentioned disadvantages, in particular to provide a device for extracorporeal blood treatment which can be produced at optimum conditions in terms of production, assembly and costs and is resistant to wear.

This object is achieved with the features of the independent claim.

A device according to aspects of the invention for extracorporeal blood treatment, in particular dialysis machine, comprises a peristaltic pump for conveying fluid from a low-pressure side to a high-pressure side and comprising a rotor which is rotatable around a rotor axis and a support area which is formed around the rotor axis in arcuate manner, with an elastically deformable fluid line being able to be positioned between the rotor and the support area and being deformed between the rotor and the support area with rotation of the rotor while forming a cross-sectional constriction, so that upon rotation of the rotor with respect to the support area a fluid in the fluid line is conveyed from the low-pressure side to the high-pressure side, the device comprising a machine housing realized as a formed sheet metal part, wherein the support area is formed in the machine housing or in a machine housing element or part by plastic deformation, in particular is formed in one piece with the machine housing or machine housing element or part.

According to aspects of the invention, the support area which can also be referred to as a running surface is integrated in the machine housing, in particular is realized in one piece with the machine housing or at least with a formed sheet metal part of the machine housing, for instance a machine front. Consequently, the number of the individual parts which have to be mounted, stored and managed during assembly of the blood treatment device, is relatively low in an advantageous manner, simplifying the assembly and organization and minimizing costs.

Furthermore, the support area is particularly stable and firm, on the one hand due to the fact of being realized in one piece with the housing, and on the other hand because of material hardening usually coming along with plastic deformation, minimizing wear and tear. In particular, the support area has a higher stiffness than a conventional support area made of plastics. The effort in terms of production engineering existing in the manufacturing of the machine housing is not greatly increased by the formation of the support area, as said housing can be prepared for receiving further functional components such as switches, displays, electric or hydraulic connections, a drive unit for the rotor, a cover for closing the pump after having inserted the elastic fluid line, etc., for instance by plastic deformation, stamping, drilling etc. In summary, one advantage achieved with the invention lies in a high functional integration and a resulting cost reduction of the machine. Finally, any electrostatic charge which may occur with adverse effects in the operation of conventional peristaltic pumps, in particular those which have a support area made of plastics or a metallic support area which is not formed in one piece with the machine housing, can be minimized.

The peristaltic pump of the device according to aspects of the invention conveys a defined volume of a medium, such as e.g. blood or dialysis fluid, from the low-pressure side, usually the arterial side, to the high-pressure side which is the venous side as a rule. The elastic fluid line is inserted in it between the rotor and the support area so as to form a loop. The rotor and the support area supporting the elastic fluid line are formed and adapted to each other such that a conveying path is defined between them. In the extension of the latter, the rotation of the rotor around the rotor axis brings about the elastically deformable fluid line being deformed and pinched off. The rotor is designed such that the fluid line is squeezed together only locally or in portions. By way of example, it may be provided with squeezing elements which are pretensioned against the fluid line and/or can be positioned relative to the rotor axis. The squeezing point brought about by the contact with the rotor travels with the rotor during its rotation and moves, so to speak, through the fluid line from the low-pressure side to the high-pressure side. As a consequence, the fluid is pressed out of the fluid line in the direction of conveyance. The replenishing fluid is sucked into the line by the low pressure, in particular the vacuum, which is produced due to the elastic recovery of the fluid line after having been deformed by the rotor. The elastically deformable fluid line may be a hose, for instance.

In the area of the conveying path, the fluid line is deformed in the previously described manner and squeezed together in a substantially fluid-tight manner with proper functioning. The squeezing elements may be directly formed on the rotor, in particular in one piece with the rotor. Alternatively, they may be arranged on rotor arms. The squeezing elements may be designed in particular as squeezing rollers or pressing rollers which advantageously roll off on the fluid line so as to protect the material, or as sliding shoes which slide over the fluid line. The squeezing elements can be able to be positioned in particular in radial direction and they can be prestressed in radial outward direction, i.e. into a position in which the fluid line is squeezed together. It is preferred that this pre-stressing process is performed with spring elements.

The invention is able to achieve in particular the following advantages:
- a higher functional integration of the machine housing, e.g. of a front door,
- a resulting cost reduction of the machine,
- an improved stiffness of the support area with respect to a support area integrated in plastics,
- a behavior in terms of electrostatic discharge (ESD) which is better than in prior art.

Advantageous embodiments of the invention are claimed in the sub-claims and will be explained in more detail below.

According to one embodiment, the support area may be formed in the machine housing, in particular in a sheet metal part forming a machine front, by cold working, in particular by deep-drawing. In this way, the formation of the support area can be integrated without big effort in a common process of manufacturing the machine housing or at least parts thereof.

According to a further embodiment of the invention, the support area may be formed at the periphery of an indentation incorporated in the machine housing. This has the advantage that the fluid pump—which will be arranged in said indentation later on—is at least partially, preferably fully integrated and/or flush-mounted in the machine front and in this way is accommodated and protected. Due to the flush-mounted rotor, the safety of the user is enhanced and the pump, in particular the rotor, is better protected from external influences.

Alternatively, the support area can be formed at the periphery of an elevation incorporated in the machine housing. By way of example, a bead comprising the support area may protrude from the sheet metal plane of the housing, allowing for a simple arrangement of the elastic fluid line.

The support area may be formed preferably as a partial cylinder. In particular, the support area may be formed so as to be inclined by an angle α with respect to the sheet metal plane of the machine housing, wherein the angle α may lie in a range between approximately 120° and approximately 95°, preferably between approximately 115° and approximately 100°, particularly preferred between approximately 110° and approximately 105°.

According to one embodiment of the invention, the support area may surround a bottom portion or bottom area which is radially formed within the support area and is deformed in particular together with the support area. According to one embodiment of the invention, the bottom portion or bottom area may define an axial bearing surface for the fluid line and/or the rotor. The bottom portion may be formed with respect to the support area so as to be substantially at least partially orthogonal. With the embodiment described above, it is particularly easy to lay the elastic fluid line on the machine housing without any kinks or sharp changes in direction and to place it in the indentation comprising the support area. Here, a fluid flow through the fluid line is subjected only to substantially smooth and small changes in direction, minimizing flow resistances in the line.

The rotor axis is formed and oriented so as to be preferably parallel to the support plane. This ensures that the elastic fluid line is squeezed together in the best possible manner.

It is preferred that the indentation comprises an essentially horseshoe-shaped outer contour, wherein inlet faces are formed at both sides of the support area so as to be preferably parallel to the rotor axis. Advantageously, the fluid line will be slowly deformed by the rotor in the area of these inlet faces, which results in an especially low stress on the material.

It can also be stated that the invention relates to a device for extracorporeal blood treatment, comprising a support or running surface which is integrated in a sheet metal housing front. Said support or running surface is part of a peristaltic pump, in particular blood pump, for instance a peristaltically working roller pump or hose pump for medical technology. In combination with the elastic material properties of the pump segment of a transition system, a rotor allows a pump function which ensures the conveyance of a fluid, in particular the conveyance of blood to a dialyzer. Here, the pump segment of the transition system is placed in the form of a loop against the cylindrical support or running surface integrated in the sheet metal housing front. Here, the support or running surface has an influence on the amount of the conveyed medium with the cylindrical diameter and the cylindrical wrap angle.

A further aspect of the invention relates to a housing part for a device for extracorporeal blood treatment, in particular dialysis machine, in particular according to any of the preceding claims, wherein the housing part is made of sheet metal. In this context, an indentation is formed in the housing part by plastic deformation, said indentation serving for receiving a rotor which is rotatable around a rotor axis and an elastically deformable fluid line section of a peristaltic pump, wherein a periphery of the indentation formed around the rotor axis in arcuate manner forms a support area against which the fluid line section can be pressed with the rotor. In this way, a housing part, e.g. a housing sheet metal wall or a housing sheet metal wall portion, forms a part of the peristaltic pump.

A further aspect of the invention relates to a method of manufacturing a housing part for a device for extracorporeal blood treatment, in particular dialysis machine, in particular according to any of the preceding aspects, comprising the steps: forming the housing part of sheet metal and forming an indentation in the housing part by plastic deformation, said indentation serving for receiving a rotor which is rotatable around a rotor axis and an elastically deformable fluid line section of a peristaltic pump, wherein a periphery of the indentation formed around the rotor axis in arcuate manner forms a support area against which the fluid line section can be pressed with the rotor for constricting the cross-section.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
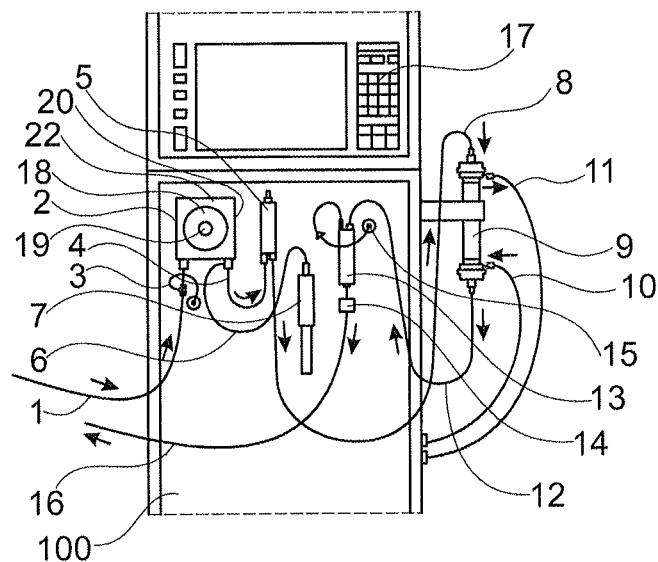
FIG. 1 is a schematic illustration of a detail of a device for extracorporeal blood treatment.

FIG. 1 exemplarily shows a detail of a device according to aspects of the invention for extracorporeal blood treatment. What is shown is essentially the entire extracorporeal blood circuit of the device. Said blood circuit comprises an arterial blood line 1 which transports blood from a (not shown) patient to a peristaltic pump 2 of the treatment device. Upstream of the peristaltic pump 2, there is provided an arterial pressure sensor 3 which measures the pressure upstream of the peristaltic pump 2, i.e. the low-pressure side pressure. At the high-pressure side of the peristaltic pump 2, a high-pressure blood line 4 goes to an arterial air catcher 5. Immediately at the outlet of the peristaltic pump 2, an additive such as heparin for blood thinning can be added via a feed line 6 and a pump 7 to the blood in the system.

From the arterial air catcher 5, a line 8 transports blood—which is under high pressure but is still untreated—to a dialyzer 9. The latter is supplied at the inlet side with dialysis liquid via a dialysis liquid feed line 10. In the dialyzer 9, the blood is treated in known manner with the dialysis liquid, e.g. is cleaned. The used dialysis liquid is removed from the dialyzer 9 via a dialysis liquid discharge line 11 and is transported to a (not shown) disposal or conditioning. The treated blood is conveyed with a blood discharge line 12 from the dialyzer 9 to a venous air catcher 13 where air is separated with an air trap 14. Provided at the venous air catcher 13 is a venous pressure sensor 15 which detects the venous pressure, i.e. the high-pressure side pressure. Coming from the air trap 14, the treated blood is returned to the patient via a venous blood line 16. FIG. 1 also illustrates a unit 17 for monitoring and controlling the device. The device for extracorporeal blood treatment is encapsulated with a housing 100 which is realized at least in parts as a formed sheet metal part.

The peristaltic pump 2 comprises a rotor 18 which rotates around a rotor axis 19. The peristaltic pump 2 further comprises a blood pump housing 20 (only schematically indicated in FIG. 1) comprising a support area 21 for an elastically deformable fluid line 22. The latter is arranged between the support area 21 of the blood pump housing 20 and the rotor 18 and is deformed during rotation of the rotor 18. At the inlet side, i.e. the low-pressure side, the fluid line 22 is connected to the arterial blood line 1, and at the outlet side, i.e. the high-pressure side, it is connected to the blood line 4. It is deformed between the rotor 18 and the support area 21 in such a manner that its cross-section is squeezed together preferably completely in the failure-free normal operation of the pump 2, i.e. is closed so as to be essentially fluid-tight.

Figure 2:
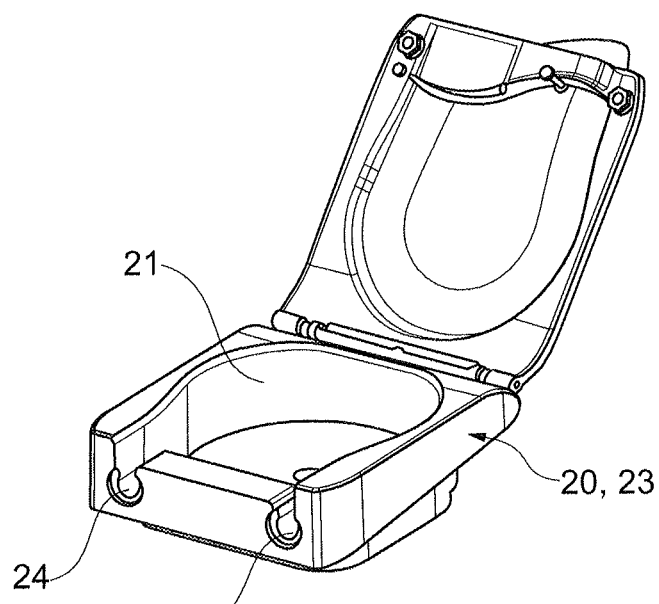
FIG. 2 is a schematic illustration of a pump housing according to the prior art.

FIG. 2 shows a blood pump housing 20 according to the prior art. Said housing is formed as a separate milled aluminum part 23 which is mounted to the housing front 100 of the apparatus. The milled aluminum part 23 is of relatively complex design and includes an inlet groove 24 and an outlet groove 25 for the fluid line 22. The support area 21 is formed in the milled aluminum part 23 by a milled indentation, resulting in a high material consumption and production expenses.

Figure 3:
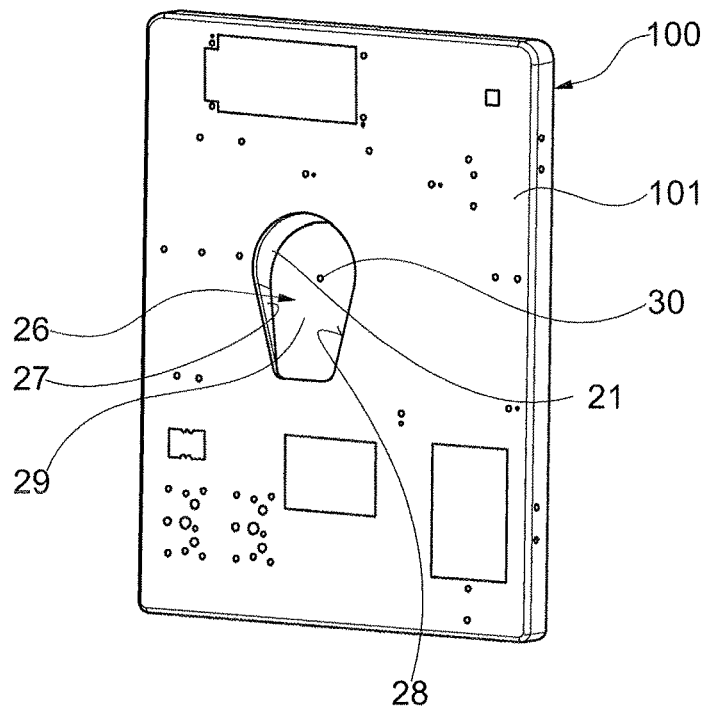
FIG. 3 is a schematic illustration of a pump housing according to aspects of the invention integrated in a machine housing, in a first perspective view.
Figure 4:
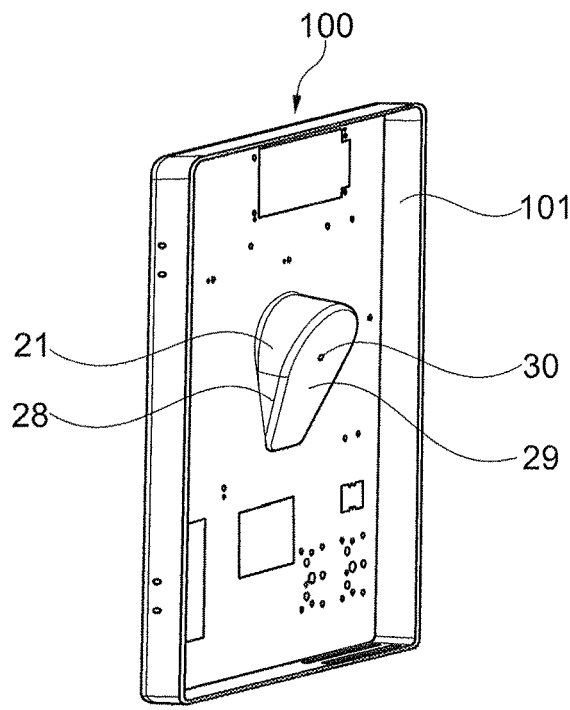
FIG. 4 shows the pump housing of FIG. 3 integrated in the machine housing, in another perspective view.
Figure 5:
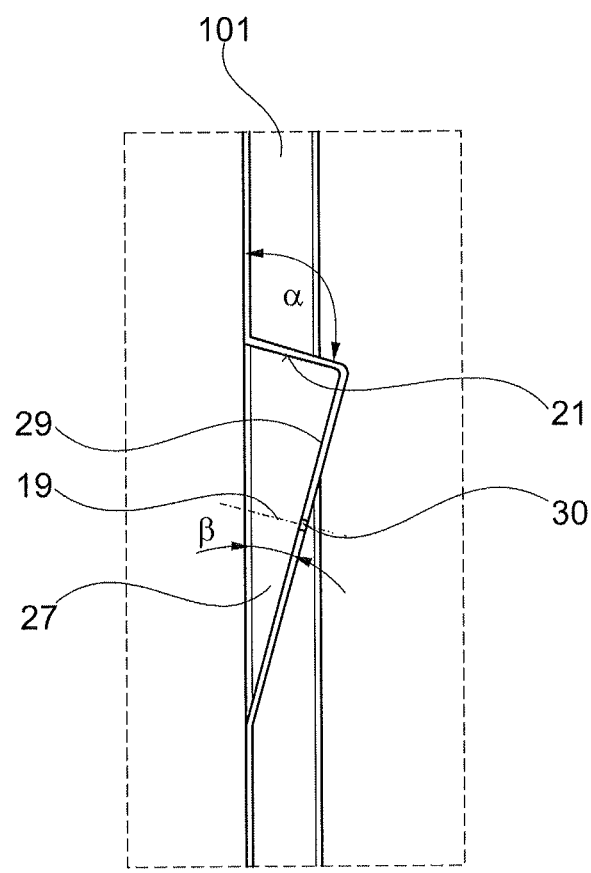
FIG. 5 shows the pump housing of FIGS. 3 and 4 integrated in the machine housing, in a cross-sectional view.

FIGS. 3, 4 and 5 show a blood pump housing 20 which according to aspects of the invention is integrated in a sheet metal 101 of the housing front 100. The support area 21 thereof is realized by producing an indentation 26 directly in the sheet metal front 101 of the apparatus housing 100 with a suitable deformation method such as deep-drawing, for example. The indentation 26 is delimited by the support area 21, an inlet-side wall 27, an outlet-side wall 28 and a bottom wall 29. With the embodiment illustrated in the Figures, the indentation 26 is formed so as to be inclined with respect to the remaining housing front (see in particular FIG. 5). This is why the support area 21 is inclined by an angle α and the bottom wall 29 by an angle β with regard to the remaining housing front. This is clearly visible in particular in FIG. 5. Said inclined arrangement serve the purpose to facilitate the installation of the fluid line 22 into and out of the pump housing 20 without any kinks in the fluid line 22 or with as small kinks as possible.

The support area 21 is designed in the form of a pitch (circle) cylinder. Its central axis coincides with the rotor axis 19 and is inclined with respect to the housing front by the angle α. An axle seating 30 is provided in the bottom wall 29 for passing the rotor axis 19 through the housing 100.

Moreover, it is also possible that further components required for the operation of the pump, such as covers, guide elements for the pump segment of the transition system and a drive unit (all not shown) are mounted or can be mounted directly on the sheet metal front.

As already indicated above, the housing front 100 is made of a sheet metal and the indentation 26 is formed therein by plastic deformation, said indentation serving for receiving the rotor 18 which is rotatable around the rotor axis 19 and the elastically deformable fluid line section 22 of the peristaltic pump 2, wherein the periphery of the indentation 26 formed around the rotor axis 19 in arcuate manner forms the support area 21 against which the fluid line section 22 can be pressed with the rotor 19 for constricting the cross-section.

The invention claimed is:

1. A device for extracorporeal blood treatment comprising:
    a rotor rotatable around a rotor axis; and
    a formed sheet metal housing part including a support area formed in the formed sheet metal housing part by plastic deformation, the support area formed around the rotor axis in an arcuate manner;
    wherein the rotor and the support area of the formed sheet metal housing part provide a peristaltic pump configured to convey fluid in an elastically deformable fluid line from a low-pressure side to a high-pressure side when the fluid line is positioned between the rotor and the support area and deformed by the rotor and the support area with rotation of the rotor which forms a cross-sectional constriction, so that upon rotation of the rotor with respect to the support area the fluid in the fluid line is conveyed from the low-pressure side to the high-pressure side, wherein the support area is inclined by an angle α of between 120° and 95° with respect to a surface plane of the formed sheet metal housing part.

2. The device for extracorporeal blood treatment according to claim 1, wherein the device is a dialysis machine.

3. The device for extracorporeal blood treatment according to claim 1, wherein the support area is formed by cold working.

4. The device for extracorporeal blood treatment according to claim 3, wherein the support area is formed by deep-drawing.

5. The device for extracorporeal blood treatment according to claim 1, wherein the support area is located at the periphery of an indentation or elevation incorporated in the formed sheet metal housing part.

6. The device for extracorporeal blood treatment according to claim 1, wherein the support area is a partial cylinder.

7. The device for extracorporeal blood treatment according to claim 1, wherein the angle α is between 115° and 100°.

8. The device for extracorporeal blood treatment according to claim 7, wherein the angle α is between 110° and 105°.

9. The device for extracorporeal blood treatment according to claim 1, wherein the support area surrounds a bottom portion or bottom area which is radially formed within the support area and is deformed with the support area.

10. The device for extracorporeal blood treatment according to claim 9, wherein the bottom portion or the bottom area forms an axial bearing surface for at least one of the fluid line or the rotor.

11. The device for extracorporeal blood treatment according to claim 1, wherein the rotor axis is parallel to the support area.

12. The device for extracorporeal blood treatment according to claim 5, wherein the indentation has a horseshoe-shaped outer contour, wherein Inlet faces and outlet faces are formed at respective sides of the support area such that they are parallel to the rotor axis.

13. The device for extracorporeal blood treatment according to claim 1, wherein an indentation is formed in the housing part by the plastic deformation, the indentation serving for receiving the rotor, wherein a periphery of the indentation formed around the rotor axis in an arcuate manner forms the support area against which the fluid line section can be pressed by means of the rotor for constricting the cross-section.

14. A method of manufacturing a device for extracorporeal blood treatment, the method comprising the steps of:
  forming a housing part of sheet metal;
  forming an indentation in the housing part by plastic deformation, the indentation serving for receiving a rotor which is rotatable around a rotor axis and an elastically deformable fluid line section of a peristaltic pump, wherein a periphery of the indentation formed around the rotor axis in arcuate manner forms a support area against which the fluid line section can be pressed by means of the rotor for constricting the cross-section; and
  rotating the rotor with respect to the support area such that the fluid in the fluid line section is conveyed from a low-pressure side to a high-pressure side, wherein the support area is inclined by an angle α of between 120° and 95° with respect to a surface plane of the formed sheet metal housing part.

* * * * *